United States Patent
Quinteros et al.

(10) Patent No.: US 11,030,438 B2
(45) Date of Patent: Jun. 8, 2021

(54) DEVICES HAVING SYSTEM FOR REDUCING THE IMPACT OF NEAR DISTANCE VIEWING ON MYOPIA ONSET AND/OR MYOPIA PROGRESSION

(71) Applicant: Johnson & Johnson Vision Care, Inc., Jacksonville, FL (US)

(72) Inventors: Ernesto Quinteros, South Orange, NJ (US); Vicente Caride, New York, NY (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 15/926,344

(22) Filed: Mar. 20, 2018

(65) Prior Publication Data
US 2019/0294861 A1    Sep. 26, 2019

(51) Int. Cl.
| | |
|---|---|
| G06K 9/00 | (2006.01) |
| A61B 3/10 | (2006.01) |
| G01C 3/06 | (2006.01) |
| G06F 3/01 | (2006.01) |
| G16H 20/00 | (2018.01) |
| G08B 21/24 | (2006.01) |

(52) U.S. Cl.
CPC .......... *G06K 9/00255* (2013.01); *A61B 3/10* (2013.01); *G01C 3/06* (2013.01); *G06F 3/013* (2013.01); *G02C 2202/24* (2013.01); *G08B 21/24* (2013.01); *G16H 20/00* (2018.01)

(58) Field of Classification Search
CPC .............................. G06K 9/00255; G01C 3/06
See application file for complete search history.

(56) References Cited

U.S. PATENT DOCUMENTS

| | | | | |
|---|---|---|---|---|
| 8,170,621 | B1* | 5/2012 | Lockwood | H04W 52/0254 |
| | | | | 455/566 |
| 9,690,372 | B2 | 6/2017 | Ji et al. | |
| 2004/0227992 | A1* | 11/2004 | Putilin | H04N 13/117 |
| | | | | 359/462 |
| 2008/0088936 | A1* | 4/2008 | Tang | G02B 27/0172 |
| | | | | 359/630 |
| 2009/0197615 | A1* | 8/2009 | Kim | H04M 1/605 |
| | | | | 455/456.1 |

(Continued)

FOREIGN PATENT DOCUMENTS

| | | |
|---|---|---|
| CN | 201689437 | 12/2010 |
| RU | 166675 | 12/2016 |

(Continued)

*Primary Examiner* — Solomon G Bezuayehu (57) ABSTRACT

The present invention is directed to a system that may be incorporated into currently available electronic devices such as laptops, cell-phones and tablets, that help the user to maintain a viewing distance that is safe for the eyes. In order to avoid near-point stress on the eyes which may lead to the onset of myopia and/or accelerate the progression of myopia, especially in children or young adults, the system of the present invention monitors viewing distance and automatically distorts the image and/or text display into a format that is unreadable, for example, through blurring or pixilation, when the device is too close to the viewer. Alternatively, the system may automatically turn off the display when the device is too close and turn the display on when the device is at the proper viewing distance.

11 Claims, 4 Drawing Sheets

(56) References Cited

U.S. PATENT DOCUMENTS

| | | | |
|---|---|---|---|
| 2011/0237999 A1* | 9/2011 | Muller | A61B 3/107 604/20 |
| 2013/0005443 A1* | 1/2013 | Kosta | A63F 13/20 463/25 |
| 2013/0194663 A1* | 8/2013 | Saigo | G02B 27/2228 359/464 |
| 2014/0135070 A1* | 5/2014 | Shi | G06F 1/3231 455/566 |
| 2014/0285429 A1* | 9/2014 | Simmons | G02B 27/0172 345/156 |
| 2015/0179150 A1* | 6/2015 | Andrysco | G06F 3/005 345/156 |
| 2015/0253971 A1* | 9/2015 | Nakamura | G09G 5/00 345/661 |
| 2015/0264299 A1* | 9/2015 | Leech | G06F 3/013 348/78 |
| 2016/0026241 A1* | 1/2016 | Leung | H04M 1/72569 345/156 |
| 2016/0066036 A1* | 3/2016 | Felt | H04N 21/4542 386/241 |
| 2016/0139662 A1* | 5/2016 | Dabhade | G06F 1/1686 345/156 |
| 2016/0373645 A1* | 12/2016 | Lin | H04N 5/23219 |
| 2017/0199385 A1 | 7/2017 | Kong | |
| 2017/0345393 A1 | 11/2017 | Wu et al. | |
| 2018/0048882 A1 | 2/2018 | Eash et al. | |
| 2018/0167613 A1 | 6/2018 | Hannuksela et al. | |
| 2018/0308455 A1* | 10/2018 | Hicks | G09G 5/377 |
| 2018/0349651 A1 | 12/2018 | Snediker et al. | |
| 2019/0227636 A1* | 7/2019 | Lopez Gil | G06F 3/147 |
| 2019/0252054 A1* | 8/2019 | Dirani | G06F 9/451 |
| 2020/0174277 A1* | 6/2020 | Karafin | B29C 64/241 |

FOREIGN PATENT DOCUMENTS

| | | |
|---|---|---|
| WO | WO2018/009144 A1 | 1/2018 |
| WO | WO2018014960 | 1/2018 |

\* cited by examiner

DEVICES HAVING SYSTEM FOR REDUCING THE IMPACT OF NEAR DISTANCE VIEWING ON MYOPIA ONSET AND/OR MYOPIA PROGRESSION

BACKGROUND OF THE INVENTION

1. Field of the Invention

The present invention relates to two-dimensional electronic displays, and more particularly, to two-dimensional electronic displays incorporating a combination of hardware and software for establishing safer viewing distances to reduce the incidence of near-point stress and thereby reduce the onset of myopia and/or reduce the likelihood of myopia progression caused thereby.

2. Discussion of the Related Art

Myopia or nearsightedness is an optical or refractive defect of the eye wherein rays of light from an image focus to a point before they reach the retina. Myopia generally occurs because the axial length of the eyeball globe is too long or the anterior surface of the cornea is too steep. Myopia affects up to thirty-three (33) percent of the population of the United States and in some parts of the world, up to seventy-five percent of the population. The cause of this refractive error is not specifically known; however, it is most likely due to a combination of genetic factors, for example, eye globe size and corneal curvature, and environmental factors, including adaptive environmental stress. A minus powered spherical lens may be utilized to correct myopia. The minus powered lens diverges the incoming light rays thereby moving the focal point of the image back onto the macula. As set forth herein, these corrective lenses treat myopia, but do not prevent the progression of myopia.

Myopia progression is fueling dramatic increases in the condition. As an example, sixty years ago, approximately fifteen (15) percent of the Chinese population was nearsighted. That percentage today is close to 90 percent for teenagers and young adults. And while this is reaching epidemic proportions in Asia, increases are also taking place in Europe and the United States where approximately half of young adults are likely near sighted.

A number of methods to slow or retard myopia progression, especially in children, have been proposed and developed. These methods including utilizing multi-focal lenses, utilizing lenses with one or more aberrations introduced therein, utilizing lenses which control aberrations, utilizing off axis power lenses, reshaping the cornea, exercising the eye and utilizing pharmacological or drug therapies. Specifically, atropine, a non-selective muscarinic agent, has been shown in a number of studies to be useful in the treatment of myopia.

The use of multi-focal lenses and those having aberrations have proved to be somewhat disadvantageous in that the lenses may compromise the wearer's distance vision and have limited treatment efficacy of around thirty (30) percent to fifty (50) percent of axial elongation or refractive difference to age matched control group as shown in a number of published studies. The other methods set forth above also suffer from disadvantages, including discomfort, as with the corneal reshaping, and potentially undesirable side effects, as with the pharmacological or drug therapies.

The above described solutions focus on devices and/or therapeutic agents that directly impact the eyes of an individual without addressing external environmental concerns that may impact myopia onset and/or progression. One such environmental concern is the accommodative stress from viewing images produced by electronic displays too closely. Accordingly, there exists a need for a system for automatically establishing safer viewing distances of electronic displays to avoid near-point stress.

SUMMARY OF THE INVENTION

The displays having a system for reducing the impact of near distance viewing on myopia onset and/or myopia progression of the present invention overcomes a number of disadvantages associated with the current state of the art.

In accordance with one aspect, the present invention is directed to a system for reducing the impact of near distance viewing on at least one of myopia onset and myopia progression. The system comprising an electronic display, a range finder operatively associated with the electronic display and configured to determine the distance between a user and the electronic display, a display controller operatively associated with the electronic display, and a microprocessor in communication with and configured to coordinate the operation of the range finder and the display controller, wherein the microprocessor is configured to automatically disrupt the display via the display controller when the display is too close to the user and automatically restoring the image when the display is at a proper viewing distance.

In accordance with another aspect, the present invention is directed to a method for reducing the impact of near distance viewing on at least one of myopia onset and myopia progression. The method comprising the steps of calculating the distance between a user and an electronic display, automatically disrupting an image displayed on the electronic display when the calculated distance between a user and the electronic display is below a predetermined threshold, and automatically restoring the image displayed on the electronic display when the calculated distance between a user and the electronic display is at or above the predetermined threshold.

One of the risk factors for myopia development and myopia progression is near work. Due to accommodative lag or negative spherical aberration associated with accommodation during such near work, the eyes may experience hyperopic blur, which in turn stimulates myopia progression. Hyperopic blur or defocus is known to lead to predictable, in terms of both direction and magnitude, changes in eye growth, consistent with the eyes growing to compensate for the imposed defocus. Hyperopic blur results in the thinning of the choroid and an increase in the scleral growth rate which results in myopic refractive errors. Moreover, the accommodation system is an active adaptive optical system which is impacted by optical devices as well as the working distance. The present invention is simple and easy to implement solution to near-point eye stress which in turn preferably reduces the incidence of and/or progression of myopia.

The present invention is directed to a system that may be incorporated into currently available electronic devices such as laptops, cell-phones and tablets, that help the user to maintain a viewing distance that is safe for the eyes. In order to avoid near-point stress on the eyes which may lead to the onset of myopia and/or accelerate the progression of myopia, especially in children or young adults, the system of the present invention monitors viewing distance and automatically distorts the image and/or text display into a format that is unreadable, for example, through blurring or pixilation, when the device is too close to the viewer. Alternatively, the system may automatically turn off the display when the device is too close and turn the display on when the device is at the proper viewing distance.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The present invention is directed to a system that enables a user to view two-dimensional electronic displays from a distance that minimizes the effects of chronic near-point stress on the muscles of the eye. Asthenopia is the technical term for a weakness or fatigue of the eye and it may be classified as accommodative asthenopia which arises from a strain of the ciliary muscle or muscular asthenopia which arises from a strain of the extra-ocular muscles. Both forms may result from reading or concentrating on images presented on a two-dimensional display too closely. Minimizing the effects of near-point eye stress is important because near-point eye stress may have a negative impact on eye health, particularly in children and young adults. Refractive status is influenced by vision development, adaptation to environmental stress and hereditary factors such as eye globe size and shape. Accordingly, repeated near-point eye stress may impact a child's or young adult's refractive development as they are more susceptible to environmental factors during development. Near-point eye stress may also adversely impact an adult's refractive development even though an adult's vision is more stable. In other words, repeated or chronic near-point eye stress may make a child and or a young adult myopic and/or accelerate the progression of myopia, and to a lesser extent the same result may be found in adults.

Near-point stress as the name suggests is simply stress on the human visual system due to near work, for example, reading. The human visual system, anthropologically speaking, was designed for distance work; namely, hunting and gathering. The industrial revolution represented a turning point in human development, wherein individuals shifted from distance work to near vision work and our anatomy has not yet fully adapted to this change. Essentially, near work does not allow our eyes to relax and ultimately this strain may cause myopia and/or accelerate myopia progression, especially in children and young adults.

The use of digital or electronic devices, for example, tablets and electronic readers world-wide has significantly increased over the last decade. The use of laptops, tablets, electronic readers, phones as well as other hand-held electronic and desktop devices with two-dimensional displays has affected the lives of adults and more significantly the lives of children and young adults given that it permeates almost every aspect of their lives, for example, recreational uses through gaming and social media and educational activities such as reading. Since it is apparent that these devices are now the norm rather than the exception, they should be utilized in the proper manner; namely, by using them at the proper or safe viewing distance to avoid and/or to minimize near-point eye stress. The generally accepted or proper reading or viewing distance is between fourteen (14) and sixteen (16) inches from the eyes to avoid near-point stress. Accordingly, the present invention is directed to a system that may be incorporated into any electronic hand-held or desk top device that includes a two-dimensional display, that distorts the display in some manner when the device is held to closely to the user's eyes and restores the image when the device or user is at the proper viewing distance. In other words, as long as the device is held at the proper distance from the user's eyes, the image is clearly viewable, and when the device is too close, the image is distorted thereby forcing or prompting the user to adjust the distance. The image on the display may be distorted in any number of suitable ways. A suitable way includes any means that renders the image or text unintelligible or unrecognizable but does not in any way have a deleterious effect on the eyes of a user. It is important that the level of distortion is such that no individual, no matter what they do at their current viewing distance or closer renders the image viewable. For example, the image may be blurred or pixelated in some manner. Pixilation is preferred for the reasons set forth subsequently. The means for distorting an image is well known in the electronic display art. In an alternative exemplary embodiment, the display may simply be turned off when the device is too close to the user's eyes and turned back on when the device is at the proper viewing distance for that individual. In this exemplary embodiment, there will be no doubt as to the fact that the device or user should move. The device would automatically turn on and off without any action by the user other than maintaining a proper viewing distance.

In order to determine if the electronic device is at the proper or safe viewing distance for a particular user, the system preferably has a means for determining the distance between the eyes of the user and the display of the electronic device. Many currently available hand-held and desktop electronic devices have built in range finders, for example, infra-red range finders. Stand-alone digital cameras and/or digital cameras that are integrated into other devices such as phones have range finders to accurately determine the distance to a target for autofocusing purposes. Proper viewing distance is the key to eye health and there are many technologies available to determine the distance between a device and a user; however, in order to reduce errors in distance calculations due to the size of the individual, for example, child or adult, and/or the angle or orientation of the display relative to that of the eyes of the user, facial mapping or facial recognition systems may preferably be utilized so that the precise distance between a user's eyes and the display may be calculated rather than the distance between some portion of the user's anatomy and the display. Although different facial mapping or recognition strategies may be utilized in accordance with the present invention, one simple approach may be to identify the user's eyes, determine the position between the eyes, interocular distance, and to average the distance between each of the eyes and the display of the electronic device as is discussed in greater detail subsequently.

Facial recognition technology is part of the field of biometrics which is concerned with the measurement of biological data by a combination of hardware and software. Facial recognition technology uses software to identify or verify a person by mapping facial features, characteristics and dimensions, and comparing the collected information with information stored in a database of faces. Facial recognition systems use a number of measurements and technologies to scan faces, including thermal imaging, three-dimensional face mapping, cataloging unique features; namely, landmarks, analyzing geometric proportions of facial features, mapping the distance between key facial features and skin surface texture analysis. Facial mapping and facial recognition technologies are widely utilized in everything from governmental and commercial security systems to personal electronic devices and may be readily adapted for the purpose of the present invention.

By applying facial mapping/recognition technology and combining it with sensors for determining distance, it is possible to manage and monitor a precise safe distance from the eyes of a user to the display or screen of the electronic device. It is important to note there are numerous ways to accurately determine safe or optimal viewing distances in addition to facial mapping/recognition and they are described herein as exemplary embodiments. Alternative means include proximity sensors, accelerometers and any other suitable means for measuring distance and angles. When the system detects that the distance from the eyes of the user to the display is too close, a signal is automatically sent to scramble the image in any suitable manner as described above thereby rendering it unusable. As soon as the distance is corrected, a signal is automatically sent to restore the image. The user only has to move and maintain the minimum safe operation distance.

The facial mapping/recognition technology is preferably robust enough to accommodate various contingencies. For example, the facial mapping/recognition technology should contain a combination of hardware and software to determine interocular distance through glasses and/or tinted glasses. Simple filtering techniques, whether implemented in hardware, software or a combination thereof may be utilized to accomplish this. In addition, the facial mapping/recognition technology should preferably be able to make the necessary measurements even if the user's face is partially obscured, for example, if the user's mouth and nose are covered. It would also be preferable if the display were not distorted or shut off if the user simple passes his or her hand in front of their face while using the device. In other words, the combination of the facial mapping/recognition technology and the range finder technology should preferably be robust enough to avoid "false alarms." Once again, it should be noted that there are many alternatives for implementing this feature.

Figure 1:
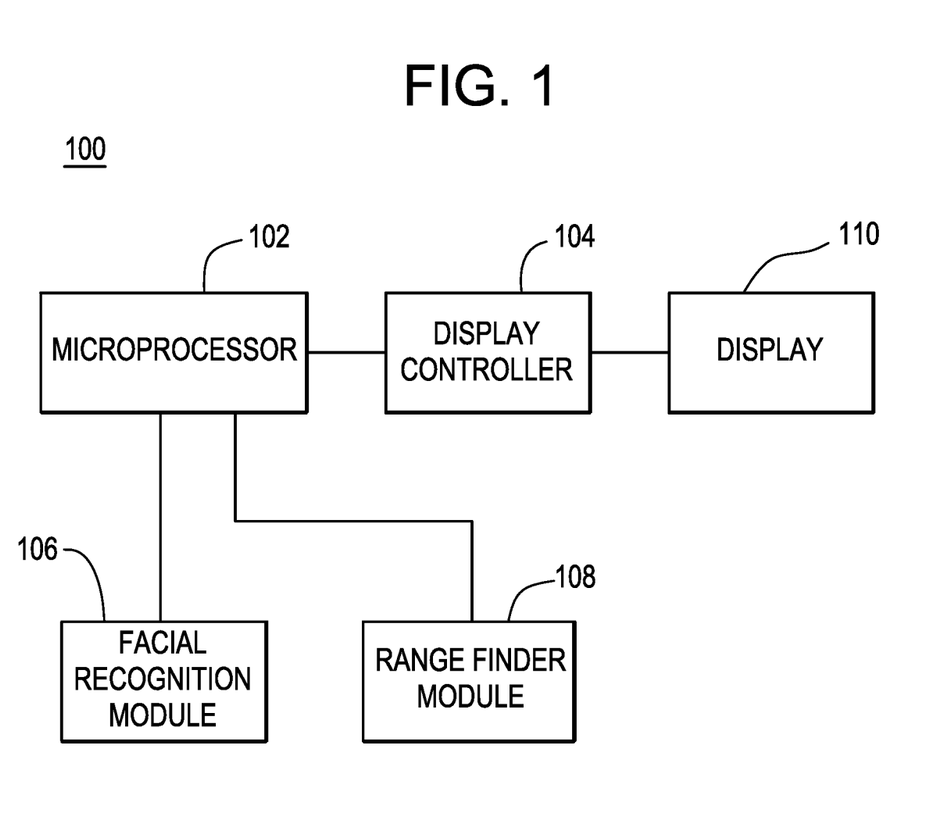
FIG. 1 is a block diagram representation of an exemplary system for reducing the impact of near point viewing in accordance with the present invention.

Referring to FIG. 1, there is illustrated a high-level block diagram representation of an exemplary system 100 for reducing the impact of near distance viewing on myopia onset and/or myopia progression. The system 100 comprises a microprocessor 102, a display controller 104, a facial recognition module 106 and a range finder module 108. It is important to note that the microprocessor 102, the display controller 104, the facial recognition module 106 and the range finder module 108 may already be integral with the electronic device as is the display 110, and the software and/or hardware updated to implement the functions of the system 100 in accordance with the present invention. In alternative embodiments, each of these elements and/or software packages may be added to the electronic device to provide the desired functionality. In an alternative exemplary embodiment, the addition of a timer may be utilized to monitor the total duration of viewing, and if a pre-established value/duration is exceeded, the image may be pixelated or otherwise distorted to limit viewing time alone or in combination with monitoring proper viewing distance. This timed usage function may also provide a warning through a pixelated flash or audible alert. The warning, which may be set to a specific duration, may be utilized to alter the user or a user's parents if the user is below a certain age, that the display will be distorted or otherwise shut off for a certain period of time in order for the user to relax his or her eyes. This would be a voluntary function that can be programmed into the system. Even though a user may be utilizing the device at the proper viewing distance, continued near work may also have a deleterious effect regarding myopia onset and progression. This warning will allow the user to take a break from the near work and allow them to participate in distance vision work or play, or simply go outside and be exposed to natural light. The timer function may be implemented in a variety of ways, including those known to those skilled in the art. For example, once the device is turned on and being operated in its intended fashion, the internal processor may run a timing subroutine that generates the alarm at the desired or preprogrammed time. The facial mapping/recognition software may be utilized to determine if the user is a child or an adult as explained in greater detail subsequently. Alternative, the user's age may be preprogrammed into the device as part of the initial setup.

The microprocessor 102 controls the overall function of the system 100. The facial recognition module 106 and the range finder module 108 under the control of the microprocessor 102 periodically, albeit with a high frequency, sends out signals to determine if the user of the electronic device is positioned at the right or optimal distance to view the display on the electronic device. If the electronic device is too close to the user, the microprocessor 102 is notified by signals from the facial recognition module 106 and the range finder module 108 and in response thereto outputs a signal to the display controller 104 to pixelate or otherwise distort the displayed image. As set forth above, some level of pixilation is the preferred manner in which to distort the image. A pixelated image provides a dramatic and clear indication that the device is too close to the user, whereas a blurry image may not be detected by a user, or possibly not noticed by the user, depending on the visual acuity of the user. Once again, pixilation is one exemplary method for distorting the image. Any suitable means may be utilized so long as the image or text is not readable and does no harm by viewing. This has the effect to prompt the user to either move the device back to a safer distance or move him or herself to a safer distance until the position of the device is fixed. Once the optimal or safe viewing distance is reestablished, the facial recognition module 106 and the range finder module 108 will send out a signal to the microprocessor 102 to have the display controller 104 return the image to a sharp and normal presentation mode on the display 110. As long as the optimal or safe distance is maintained, no action is taken by the system 100. In instances where the user is viewing dynamic images such as a video, the video may be paused, pixelated or otherwise distorted simultaneously if the signal is sent indicating the electronic device is too close to the user. Once the position of the device is corrected, the video/image will be restored.

It is important to note that all of the components comprising the system may be implemented in hardware, software and/or a combination of hardware and software. For example, the range finder module 108 may comprise a combination of hardware, e.g. infra-red and/or ultrasonic transducer emitter/detector pairs, and software to control its operation in combination with the display controller 104 and the microprocessor 102. The software may comprise algorithms to simply may distance calculations to object. The facial recognition module 106 may comprise hardware, e.g. a camera or CCD array, and software to control its operation in combination with the display controller 104 and the microprocessor 102. In an exemplary embodiment, the software may include algorithms for calculating the distance between facial features and comparing fascial features to a known set of parameters. The display controller 104 may also comprise a combination of hardware and software to implement its functionality.

In accordance with another exemplary embodiment, the system may include the required hardware, software and/or a combination thereof to allow a user to highlight, zoom in or out, and/or to move text or images around on the display so that the user does not have to adjust his or her distance from the display. Simple touch screen technology that is currently available may be incorporated into the system.

Figure 2:
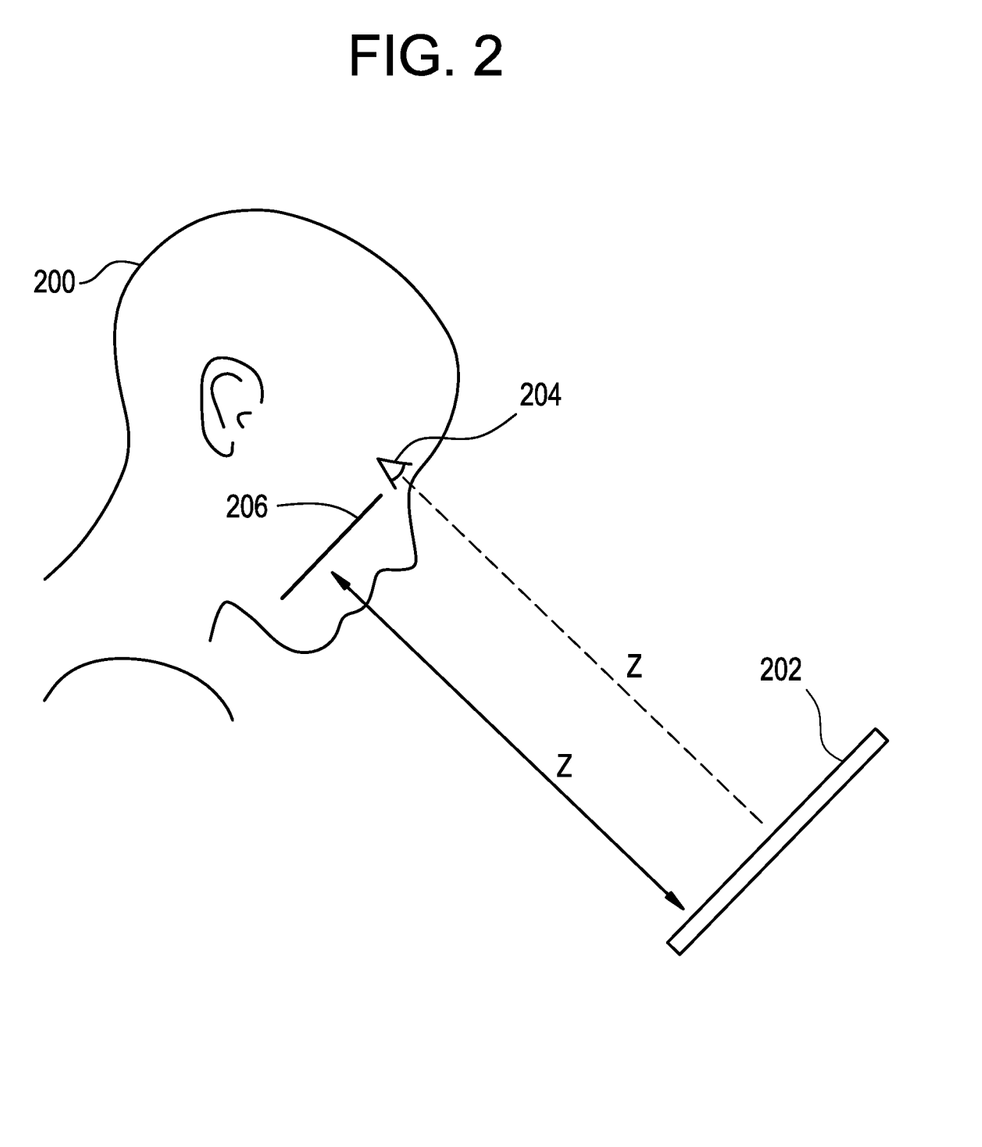
FIG. 2 is a diagrammatic representation of a user viewing an electronic device with display in accordance with the present invention.

FIG. 2 is a diagrammatic representation of a user 200 viewing a display on an electronic device 202. As illustrated, the combination of the of the facial recognition module 106 and the range finder module 108 locate and determine the distance from the eyes 204 of the user 200 to the electronic device 202. Given that both facial recognition and range finding are utilized, it is possible to form a plane across the user 200 such that the distance, Z, for the user's eyes 204 is always maintained regardless or the orientation of the electronic device and/or the user's head.

As set forth above, myopia onset and/or progression may be affected by viewing habits. The present invention comprises a content display system that utilizes the existing display and electronics, camera/rangefinder, for electronic devices such as tablets, phones and laptops, and based upon viewing distance adjusts the image such that when the display is too close to the viewer, the content, for example, text, video and/or audio is distorted and when the viewing distance is at the proper or safe amount, the content is restored. In one exemplary embodiment, the system utilizes Headtrackr. Headtrackr is a java script library for real-time face tracking and head tracking, tracking the position of a user's head in relation to a device, such as a computer screen, via a web camera and the WebRTX/getUserMedia standard. Once again, Headtrackr is only an exemplary package that may be utilized in accordance with the present invention. Any suitable software package that performs a similar function may be utilized.

Figure 3A:
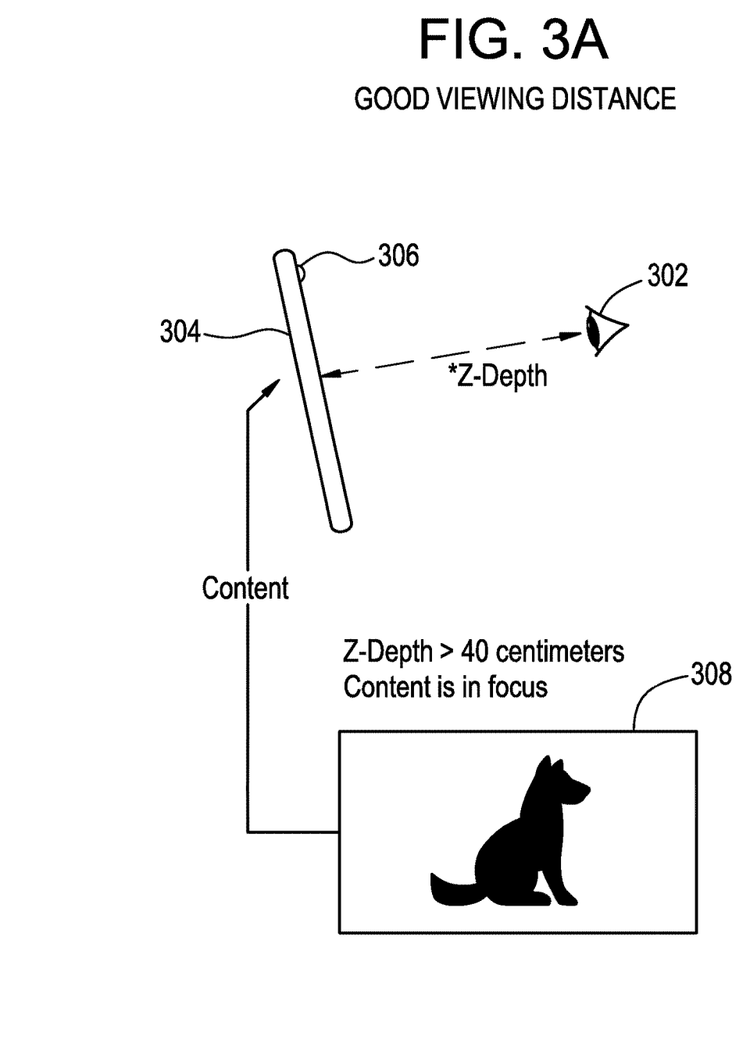
FIGS. 3A and 3B are diagrammatic illustrations of an electronic device utilized too closely and an electronic device utilized at the proper viewing distance respectively in accordance with the present invention.
Figure 3B:
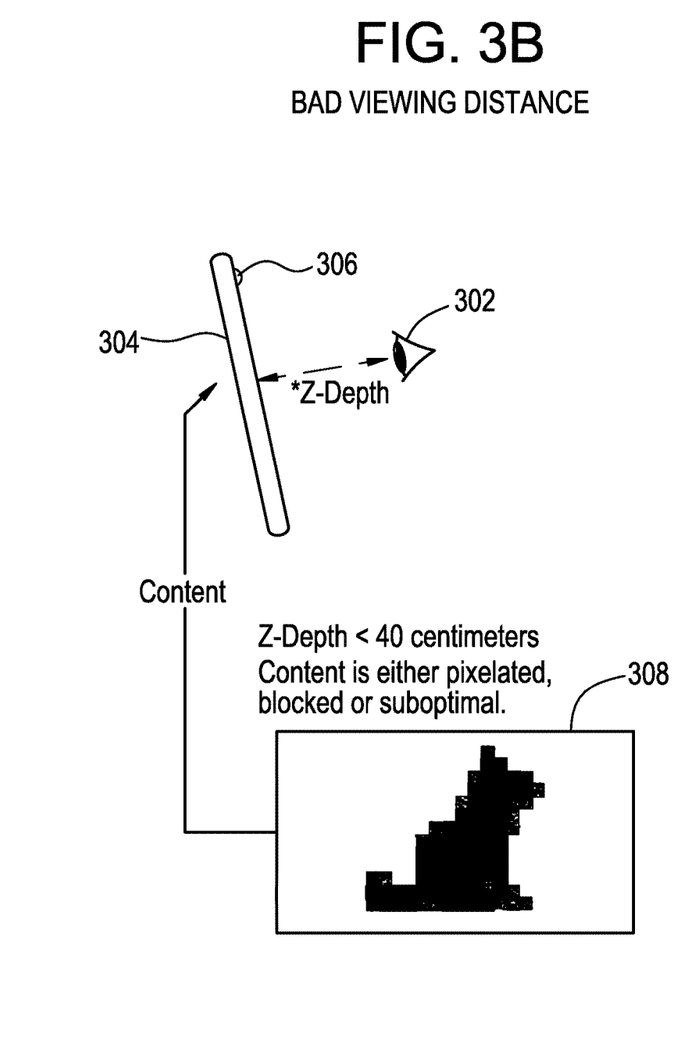

The operation of Headtrackr may be more easily understood by reference to FIGS. 3A and 3B. Utilizing HeadTrackr, the distance Z from a user's eye 302 to a display screen 304 of an electronic device having a camera or distance sensor 306. Based on the data point, Z, the system of the present invention is able to make contextual changes to the content as discussed herein. As may be easily seen, if the user's eye 302 is greater than 40 cm (between 14 and 16 inches) from the device 304, the image 308 is clear. If on the other hand the user's eye 302 is less than 40 cm from the device 304, the image is distorted.

In accordance with one exemplary embodiment, the measured value may be mapped onto a CSS filter, well known in the art. The CSS filter can provide visual effects such as blur or color shifting to render an image sub-optimal. A threshold value for the distance Z may be established such that when the display is too close, the system will swap out the high-resolution text or video to a low or pixelated display/resolution, then return to normal when the device is above the threshold distance. The same system may be utilized for sound using the same concepts set forth herein. In addition, as set forth above, additional coordinates or dimensions X and Y may be obtained to determine the user's exact position relative to the device as is explained in greater detail below.

Figure 4A:
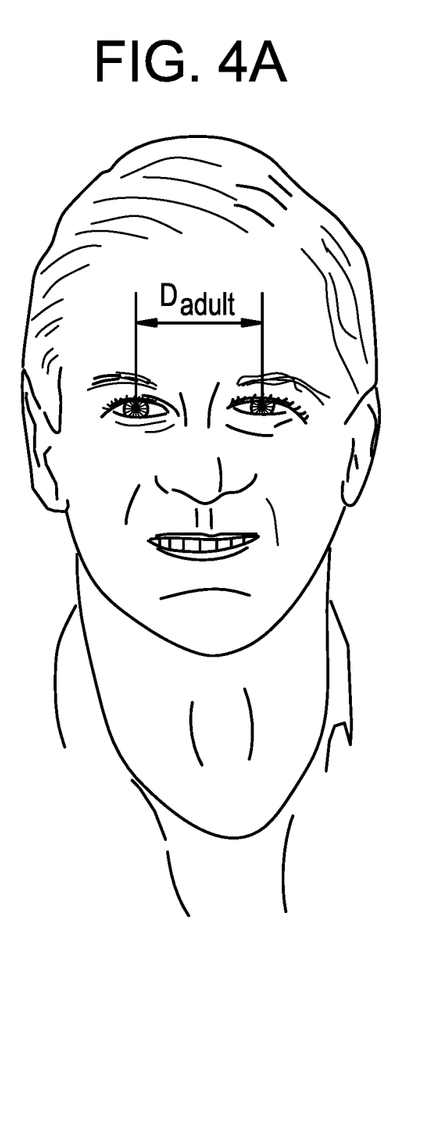
FIGS. 4A and 4B are diagrammatic representations of an adult's face and a child's face respectively mapped in accordance with the present invention.
Figure 4B:
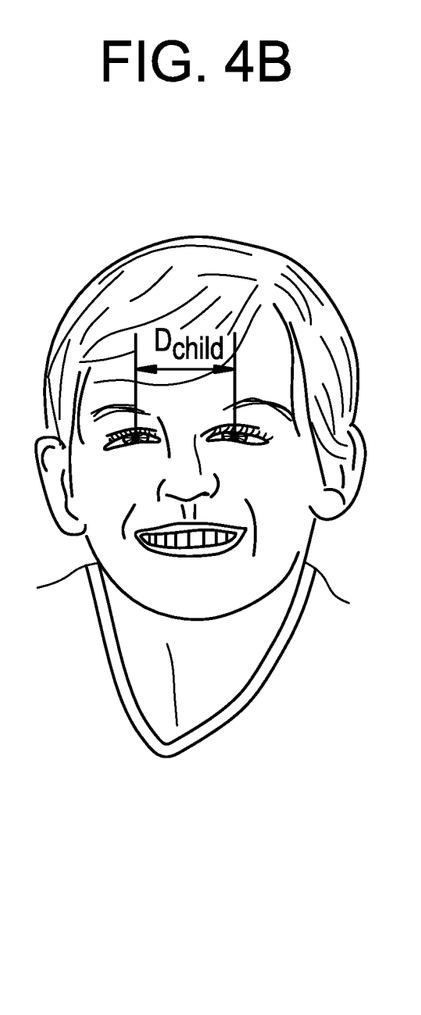

FIGS. 4A and 4B are diagrammatic representations of an adult's face and a child's face respectively mapped in accordance with the present invention. The two faces are side-by-side to highlight the dimensional/distance mapping differences of an adult's face topography relative to a child's face topology. Differences in age may be accounted for by the system of the present invention to adjust the proper viewing distance as well as the proper viewing time. Essentially, the average pupillary distance for an adult is between 54 and 68 mm with acceptable measurement deviations generally falling between 48 and 73 mm, whereas for a child the pupillary distance is between 41 and 55 mm. Other features may be utilized in accordance with the present invention, however, pupillary distance is easily measured. $D_{adult}$ and $D_{child}$ show the respective pupillary distances respectively.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A system for reducing the impact of near distance viewing on at least one of myopia onset and myopia progression, the system comprising:
 an electronic display;
 a range finder operatively associated with the electronic display and configured to determine the distance between a user and the electronic display;
 a display controller operatively associated with the electronic display; and
 a microprocessor in communication with and configured to coordinate the operation of the range finder and the display controller, wherein the microprocessor is configured to automatically distort the display via the display controller via pixilation to thereby render it unclear to a user when the display is closer to the user than a predetermined safe viewing distance of between 14 and 16 inches and automatically restore the image when the display is at a distance greater than said predetermined safe viewing distance to thereby render the display clear to said user, the microprocessor determining the average pupillary distance of the user to determine if the user is an adult or child and adjusting the predetermined safe viewing distance accordingly.

2. The system for reducing the impact of near distance viewing on at least one myopia onset and myopia progression according to claim 1 further comprising a facial recognition module.

3. The system for reducing the impact of near viewing on at least one myopia onset and myopia progression according to claim 2, wherein the electronic display is part of an electronic device.

4. The system for reducing the impact of near viewing on at least one myopia onset and myopia progression according to claim 3, wherein the electronic device is a hand-held device.

5. The system for reducing the impact of near viewing on at least one myopia onset and myopia progression according to claim 3, wherein the electronic device is a desk-top device.

6. The system for reducing the impact of near viewing on at least one myopia onset and myopia progression according to claim 3, wherein the range finder comprises an emitter/detector pair.

7. The system for reducing the impact of near viewing on at least one myopia onset and myopia progression according to claim 3, wherein the facial recognition module comprises a camera and associated software for making facial comparison calculations.

8. The system for reducing the impact of near viewing on at least one myopia onset and myopia progression according to claim 3, wherein the facial recognition module comprises a charge couple device (CCD) array and associated software for making facial comparison calculations.

9. The system for reducing the impact of near viewing on at least one myopia onset and myopia progression according to claim 1, wherein disrupting the image comprises pixelating the image.

10. The system for reducing the impact of near viewing on at least one myopia onset and myopia progression according to claim 1, wherein disrupting the image comprises blurring the image.

11. A method for reducing the impact of near distance viewing on at least one of myopia onset and myopia progression, the method comprising the steps of:
 calculating the distance between a user and an electronic display; determining the average pupillary distance of a user to determine if the user is an adult or child;
 automatically distorting an image displayed on the electronic display via pixilation to thereby render the display unclear to said user when the calculated distance between the user and the electronic display is below a predetermined safe viewing distance of between 14 and 16 inches, wherein said predetermined safe viewing distance is adjusted based on the determined average pupillary distance; and
 automatically restoring the image displayed on the electronic display to thereby render the display clear to the user when the calculated distance between a user and the electronic display is at or above the predetermined safe viewing distance.

* * * * *